(12) United States Patent
Wallace et al.

(10) Patent No.: US 9,158,887 B2
(45) Date of Patent: Oct. 13, 2015

(54) SYSTEM AND METHOD FOR RETRIEVING AND PROCESSING METADATA

(75) Inventors: William Eric Wallace, Waterloo (CA); Laura Peters, Waterloo (CA)

(73) Assignee: Agfa HealthCare, Mortsel (BE)

(*) Notice: Subject to any disclaimer, the term of this patent is extended or adjusted under 35 U.S.C. 154(b) by 291 days.

(21) Appl. No.: 13/606,767

(22) Filed: Sep. 7, 2012

(65) Prior Publication Data

US 2014/0074985 A1 Mar. 13, 2014

(51) Int. Cl.
*G06F 15/16* (2006.01)
*G06F 19/00* (2011.01)

(52) U.S. Cl.
CPC .................................. *G06F 19/321* (2013.01)

(58) Field of Classification Search
USPC .......................................................... 709/219
See application file for complete search history.

(56) References Cited

U.S. PATENT DOCUMENTS

| | | | |
|---|---|---|---|
| 7,844,571 B2 | 11/2010 | Konig | |
| 2001/0024230 A1* | 9/2001 | Tsukahara | 348/42 |
| 2004/0034550 A1* | 2/2004 | Menschik et al. | 705/3 |
| 2004/0141661 A1* | 7/2004 | Hanna et al. | 382/305 |
| 2005/0108365 A1* | 5/2005 | Becker et al. | 709/219 |
| 2005/0207658 A1 | 9/2005 | Schofield | |
| 2007/0118540 A1* | 5/2007 | Guo | 707/100 |
| 2007/0299945 A1* | 12/2007 | Lunsford | 709/223 |
| 2008/0027908 A1 | 1/2008 | Durbeck et al. | |
| 2008/0071825 A1* | 3/2008 | Guo | 707/103 R |
| 2008/0123915 A1* | 5/2008 | Nagy | 382/128 |
| 2009/0313170 A1 | 12/2009 | Goldner et al. | |
| 2010/0049740 A1* | 2/2010 | Iwase et al. | 707/104.1 |
| 2010/0211409 A1 | 8/2010 | Kotula et al. | |
| 2011/0176712 A1* | 7/2011 | Hill et al. | 382/128 |
| 2011/0239097 A1 | 9/2011 | Bates et al. | |
| 2012/0005252 A1* | 1/2012 | Canessa et al. | 709/201 |
| 2013/0266242 A1* | 10/2013 | Dorn et al. | 382/305 |
| 2014/0010421 A1* | 1/2014 | Colaco et al. | 382/128 |

* cited by examiner

*Primary Examiner* — Kostas Katsikis
(74) *Attorney, Agent, or Firm* — Jason R. Mueller-Neuhaus; Borden Ladner Gervais LLP

(57) ABSTRACT

A system and method of retrieving metadata, the method comprising: in response to a request from a client for metadata for a set of DICOM instances, loading n DICOM instances of the set of requested DICOM instances; comparing the metadata of the n loaded DICOM instances; generating a common set of values based on the comparison of the n loaded DICOM instances; streaming the common set of values to the client; determining per-instance data for each of the n loaded DICOM instances, the per-instance data being a difference between the metadata of a DICOM instance and the common set of values; transmitting the per-instance data of the loaded DICOM instances to the client; loading additional DICOM instances of the set of requested DICOM instances; determining per-instance data for each of the additional DICOM instances; and transmitting the per-instance data of the additional DICOM instances to the client.

20 Claims, 3 Drawing Sheets

SYSTEM AND METHOD FOR RETRIEVING AND PROCESSING METADATA

FIELD

The present disclosure relates generally to systems and methods for retrieving and processing metadata. More particularly, the present disclosure relates generally to systems and methods for retrieving and processing DICOM (Digital Imaging and Communications in Medicine) header metadata in a client-server context.

BACKGROUND

Client computing devices are often used to interact with data that, at least initially, is stored on a storage medium that is not directly coupled to the client computing device. Such arrangements are not restricted to any particular field or industry.

An example of such an arrangement includes client computing devices that are used to view medical images. The medical images are generally stored on a storage medium that is not directly coupled to the client computing device. For example, the client computing device generally downloads the images from the storage medium through one or more networks.

SUMMARY

In a first aspect, the present disclosure provides a method of retrieving metadata stored on a storage medium, the method comprising: in response to a request from a client for metadata for a set of DICOM instances, the set of DICOM instances having a number, loading n DICOM instances of the set of requested DICOM instances, where n is less than the number of the set of DICOM instances; comparing the metadata of the n loaded DICOM instances; generating a common set of values based on the comparison of the n loaded DICOM instances; streaming the common set of values to the client; determining per-instance data for each of the n loaded DICOM instances, the per-instance data being a difference between the metadata of a DICOM instance and the common set of values; transmitting the per-instance data of the loaded DICOM instances to the client; loading additional DICOM instances of the set of requested DICOM instances; determining per-instance data for each of the additional DICOM instances; and transmitting the per-instance data of the additional DICOM instances to the client.

In some embodiments, the common values are generated as a binary large object (blob).

In various embodiments, the n instances correspond to a series or a sub-series.

In some embodiments, the n instances exclude unusual instances, such as for example localizer images or scout images.

In some embodiments, the transmission of the per-instance data of the n loaded DICOM instances to the client is initiated prior to loading of the additional DICOM instances.

In some embodiments, the method further comprises: receiving a request for pixel data from the client; and transmitting pixel data to the client.

In some embodiments, the method further comprises, at the client: receiving the set of common values; receiving the per-instance data; initiating a display based on the common values; receiving pixel data; and displaying the pixel data.

In another aspect, the present disclosure provides a non-transitory computer-readable storage medium encoded with instructions that cause a processor to perform a method retrieving metadata stored on a storage medium, the method comprising: in response to a request from a client for metadata for a set of DICOM instances, the set of DICOM instances having a number, loading n DICOM instances of the set of requested DICOM instances, where n is less than the number of the set of DICOM instances; comparing the metadata of the n loaded DICOM instances; generating a common set of values based on the comparison of the n loaded DICOM instances; streaming the common set of values to the client; determining per-instance data for each of the n loaded DICOM instances, the per-instance data being a difference between the metadata of a DICOM instance and the common set of values; transmitting the per-instance data of the loaded DICOM instances to the client; loading additional DICOM instances of the set of requested DICOM instances; determining per-instance data for each of the additional DICOM instances; and transmitting the per-instance data of the additional DICOM instances to the client.

In another aspect, the present disclosure provides a server for use in retrieval of metadata stored on a storage medium, the server comprising: a processor, the processor configured to: in response to a request from a client for metadata for a set of DICOM instances, the set of DICOM instances having a number, load n DICOM instances of the set of requested DICOM instances, where n is less than the number of the set of DICOM instances; compare the metadata of the n loaded DICOM instances; generate a common set of values based on the comparison of the n loaded DICOM instances; stream the common set of values to the client; determine per-instance data for each of the n loaded DICOM instances, the per-instance data being a difference between the metadata of a DICOM instance and the common set of values; transmit the per-instance data of the loaded DICOM instances to the client; load additional DICOM instances of the set of requested DICOM instances; determine per-instance data for each of the additional DICOM instances; and transmit the per-instance data of the additional DICOM instances to the client.

In some embodiments, the common values are generated as a binary large object (blob).

In various embodiments, the n instances correspond to a series or a sub-series.

In some embodiments, the n instances exclude unusual instances, such as for example localizer images or scout images.

In some embodiments, the processor is further configured to initiate the transmission of the per-instance data of the n loaded DICOM instances to the client prior to loading of the additional DICOM instances.

In some embodiments, the processor is further configured to: receive a request for pixel data from the client; and transmit pixel data to the client.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the accompanying figures.

DETAILED DESCRIPTION

Figure 1:
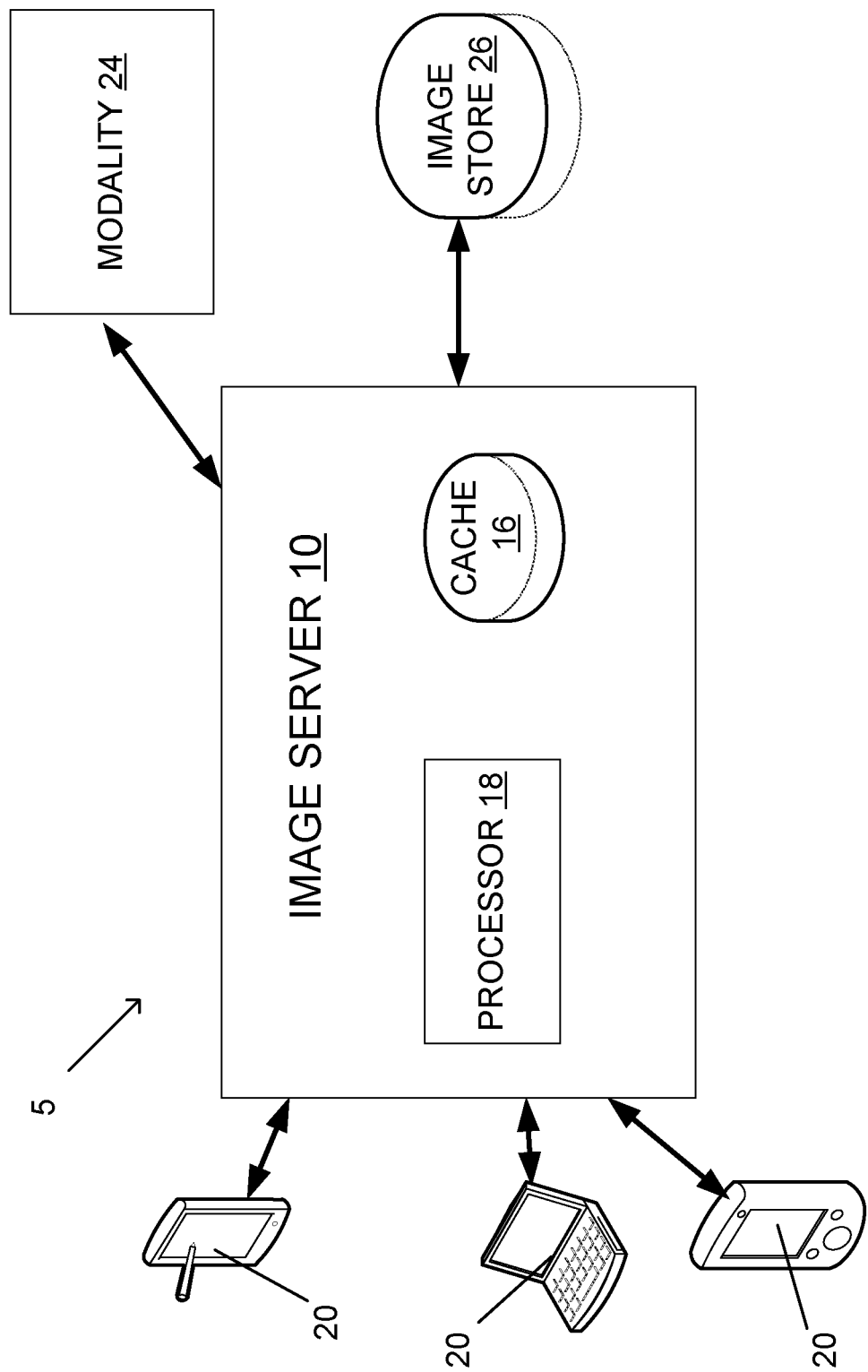
FIG. 1 is a block diagram of a metadata retrieval system, according to various environments.

For simplicity and clarity of illustration, reference numerals may be repeated among the figures to indicate corresponding or analogous elements. Numerous details are set forth to provide an understanding of the embodiments described herein. The example embodiments may be practiced without these details. In other instances, well-known methods, procedures, and components have not been described in detail to avoid obscuring the embodiments described. The description is not to be considered as limited to the scope of the example embodiments described herein.

Various embodiments disclosed herein generally relate to systems and methods for efficiently generating, retrieving, and transmitting metadata in response to requests for metadata from a client. Various embodiments disclosed herein generally relate to the requesting of metadata and the handling of received metadata. Some embodiments disclosed herein generally relate to the handling of requests for metadata and the processing of requested metadata.

Some embodiments disclosed herein relate to image metadata retrieval systems and methods. Some embodiments disclosed herein relate to medical image metadata retrieval systems and methods.

Medical images are often generated by medical modalities during patient examination. These images are then stored and later viewed by a user, such as, for example a radiologist, on a client computing device. When a modality is used to perform the patient examination, the modality generally generates a set of images, which is referred to as a "study". Each study corresponds to a given patient and includes a number of instances. In some embodiments, an instance includes, but is not limited to, an individual image, a multiframe (which can include multiple images), non-image data (e.g. data that should be applied to a referenced DICOM image such as measurements, annotations, rotations, flip, cropping, etc), or other non-image data such as a report. Accordingly, in some implementations, the medical images are generally organized in a hierarchy that corresponds to: patient-study-series-instance.

The studies generated by modalities today are, in general, larger than the studies that were generated in the past. For example, as technology advances modalities are producing more and more data per acquisition. It seems to be a trend that studies will continue to grow in size. The studies are larger in the sense that each study generally has a greater number of images and also that each image includes a greater amount of data. For example, CT scans generally contain more slices and mammography images generally contain more pixels as compared to the past. In addition, some fields in medicine, such as pathology, that previously were not digitized are now being digitized. Accordingly, there is a large amount of data (e.g. large number of image files) being stored at, for example, an image server. These files have metadata associated with them, such as, for example, DICOM metadata.

A challenge faced by image viewing systems is that in order to achieve acceptable performance levels from the perspective of each user, the DICOM metadata generally needs to be efficiently retrieved by a client from a server that may not be located on a local high-speed network. This challenge becomes increasingly difficult in light of the trends discussed above.

In addition, the determination of how to present the study and the initialization of rendering components can be quite intensive and "expensive" from the point of view of computing resources and time. For example, it can be processor (e.g. "cpu") intensive and memory intensive. However, it can also take a significant amount of time to process all of the associated data.

This burden can potentially be reduced if it is possible to have all the relevant metadata information pertaining to the images before actually retrieving the pixel data itself. Combining the metadata of all instances in a series and removing the redundancies can greatly reduce the size of the data that needs to be sent over a communication channel, such as a network. Such a combination can also reduce parsing time and memory sizes. This can translate in a performance optimization especially in high latency or low bandwidth networks. However, to create such an object requires all DICOM instances for the series to be loaded and processed, to be able to correctly remove all the redundancies; this is a very performance heavy operation.

Accordingly, various embodiments disclosed herein are directed to providing metadata that is relevant for all instances in a study when not all instances are available yet. An example of such a situation is when information is still being uploaded from a third party PACS (Picture Archiving and Communication System).

In some known systems, data blobs (binary large objects) are pre-generated which means that when a request for the data is made, no processing time is needed for removing redundancies given that this has already been done. However, generating this data blobs is very IO, processor and memory intensive and is thus a time consuming task because in order to perform this task all the DICOM instances are read and compared before the data blob is generated. Accordingly, generating such a blob in response to a request (i.e. after the request has been received) would result in a very significant delay before any data could be sent to the requester.

The pre-generation of the data blob for metadata where the redundancies are removed can work well when the data is stored in a native system and full control can be maintained over the data. However, when the data must be retrieved from a third party system, such a data blob would not exist and would need to be generated upon request, which as explained above, can lead to significant delays. This blob may need to be generated, for example, because a third party server may organize, maintain, and processes data differently than a local image server. Accordingly, in such a situation the blob could generally be generated by the local system so that the blob would work with the local system. In general, the blob may need to be regenerated each time a study (or a portion) of a study is retrieved from a third party server. This can be the case because the data stored on the third party server may change between a first retrieval of the study and a subsequent retrieval of the study. For example, instances may be added to the study or annotations and remarks may be added.

In some embodiments described herein, when a local server retrieves the instances from the third party server, the instances are retrieved one by one. DICOM allows study, series, and instance level retrieves. However, study and series level retrieves are unordered, and if another mechanism is used such as WADO retrieves, they are done one at a time. The local server starts to build the blob data. The server also starts to stream the blob data to the client. In this manner, the local server can stream the blob to the client while the local server is still receiving instances from the third party data. This allows for tasks to be completed in parallel, which in some embodiments can result in improved performance.

Reference is first made to FIG. 1, which is a block diagram illustrating the components of a system 5, in accordance with various example embodiments. System 5 includes an image server 10 and one or more clients 20. Image server 10 includes a cache 16 and a processor 18. In various embodiments, cache 16 comprises a physical memory device. Cache 16 can be used to store images retrieved from image store 26. One or more clients 20 can be coupled to image server 10 in any appropriate manner. For example, a given client 20 can be coupled to image server 10 through one or more networks, which may include, for example, the internet or an intranet. Alternatively, client 20 can be coupled to image server 10 through a direct connection. Client 20 can be any appropriate computing device, including but not limited to a desktop computer, a laptop computer, a tablet computer, and a smartphone.

In some embodiments, image server 10 is coupled, in any suitable manner including but not limited to a network as described above, to modality 24, which can be any appropriate modality including, but not limited to, any suitable image data generating device (e.g. computed radiography (CR) systems, computed tomography (CT) scanners, magnetic resonance imaging (MRI) systems, positron emission tomography (PET), mammography systems, ultrasound systems, etc.) utilized to generate image data that corresponds to patient medical examinations. In some embodiments, image server 10 receives image data from modality 24 and stores it in image store 26. In other embodiments, a different computing device other than image server 10 is used to receive images generated by modality 24 and store them to image store 26. In some embodiments, image server 10 is coupled to one or more other image servers, each of which may be the same or different than image server 10.

The other image servers to which image server 10 is coupled may, or may not themselves be coupled to other modalities, clients, or other servers.

Image store 26 can comprise any appropriate storage medium. In some embodiments, image store 26 comprises a physical non-transitory storage medium. In various embodiments, image store 26 can include, but is not limited to, one or more, hard disk drives, flash memory devices, magnetic tape storage devices, optical storage devices, or a combination thereof. In some embodiments, image store 26 is separate from image server 10 and they are coupled through any suitable communication connection such as, for example, through a network. In other embodiments, image store 26 is collocated with image server 10. In some embodiments, image store 26 is directly coupled to image server 10. In some embodiments, image store 26 is a component of image server 10.

Figure 2:
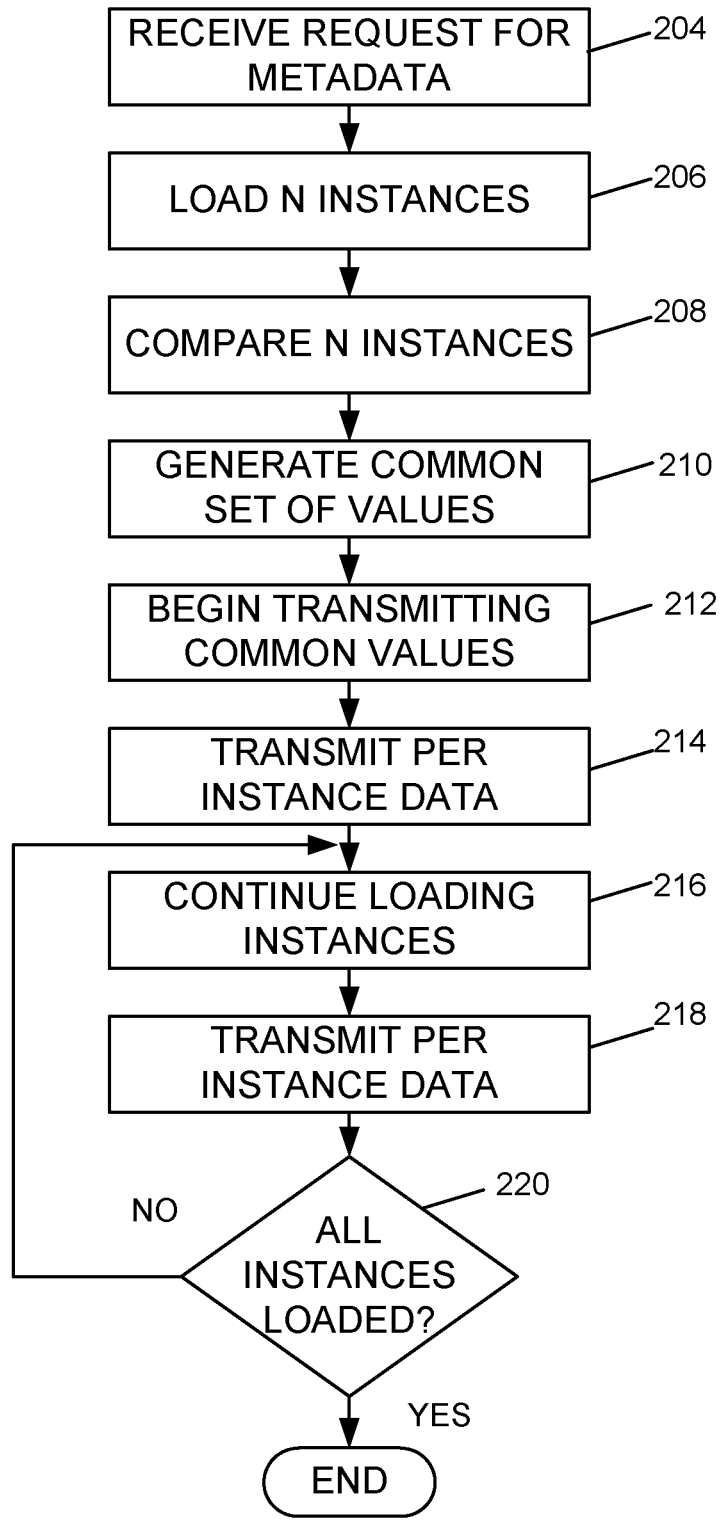
FIG. 2 is a flowchart illustrating a process by which the image server of FIG. 1 performs metadata retrieval, according to various embodiments.

Reference is now made to FIG. 2, which illustrates a flowchart diagram of the process by which image server 10 performs metadata retrieval and processing, according to various embodiments.

At 204, image server 10 receives a request for metadata from client 20. In some embodiments relating to medical imaging, the requested metadata can be, for example, for a set of DICOM instances (e.g. images).

At 206, image server 10 loads (from e.g. image store 26) n instances of the set of instances for which the metadata has been requested. In some embodiments, image server only reads the metadata. For example a DICOM instance can be thought of as a collection of tags (similar in concept to xml or html tags and can even be represented as XML) where, in the case of an image, one of the tags is the pixel data tag and its value represents the pixels. The tags of a DICOM instance, other than the pixel data tag, can be referred to as metadata. In some embodiments, when a DICOM instance is loaded by the client computer the metadata is loaded and, if available, the pixel data is separately loaded. In some embodiments, each of the tags is read except the pixel data tag in order to save memory. In principle, the pixel data tag, if present, is generally the last tag (this is by convention and if it is not the case then the DICOM is not formed according to the accepted standard) and therefore the reading is generally stopped when the pixel data tag is reached.

In various embodiments, n is less than the total number of requested images. In some embodiments, in particular if the number of requested instances is large, n will be much smaller than the total number of instances in the set of requested instances. Various embodiments can select the n instances in different ways. In some embodiments, the first n instances are selected (e.g. instances 1 to n). In some embodiments, if the first number of instances in the set of requested instances are unusual (e.g. they are not similar to the rest of the images), then those instances may be skipped and the n instances are selected from the rest of the set of requested instances. For example the first image in a series may be a localizer image, while the remaining images may be the "slices". This may be used for example, but not limited to, in CT and MR studies. The localizer image can for example be a front planar view (e.g. a projection image) of the relevant portion of the body while the slices may be the cross-sectional medical images of the relevant portion of the body. The localizer image can be used to indicate the location of a slice in the body. More specifically the localizer image and a slice can be displayed concurrently on display of client 20. The location of the slice can be indicated by, for example, a line displayed in the localizer image. As the user selects different slices for viewing, the line in the localizer image will change positions to reflect the position of the slice currently being used. As will be clear to a person of skill in the art, the "slices" will generally be similar to one another while the localizer image will generally be very different than the slices. Accordingly, in some embodiments when a localizer image is present in the requested images, the localizer image is excluded when loading the n instances.

In some embodiments, any localizer image will be treated as unusual and will be excluded. In some embodiments, the type of study is first considered and depending on the type (e.g. CT or MR studies), image server 10 checks for an unusual instance, such as a localizer image, and excludes it if present while for other types of studies image server 10 does not check for unusual instances. In this example, CT and MR studies are used as non-limiting examples.

For example, in some embodiments, if the first j instances are unusual, then the n instances may be selected to be instances i to i+n−1, where i is greater than or equal to j+1. Although in some embodiments the instances that are selected are consecutive; in other embodiments, the n selected images are not consecutive. In some embodiments, the n instances can be selected by skipping any number of instances between instances (the number of skipped instances can be constant or it can vary between selected instances). In some embodiments, the instances are selected randomly. In some embodiments, the n instances correspond to a series.

At 208, image server 10 compares the metadata associated with the n instances in order to determine the common values.

At 210, based on the comparison at 208, image server 10 generates a common set of values for metadata for the n instances that have been compared. In various embodiments, the common set of values are generated as a blob. In some embodiments, the blob comprises two tags or sequences. Tags were described above. In general, each tag can contain a value or it can contain one or more tags. When a tag contains other tags it is referred to as a sequence. In some embodiments, one sequence in the blob contains all tags that have the same value for the compared instances; while, the second sequences describes the way in which each of the instances differ from the common values.

In some embodiments described herein, the blob is generated on a series level or even a sub-series series level (e.g. one set for the scout images in an MR and one for the remaining images) rather than a study level. This may be done for several reasons. For example, the variation between two randomly selected instances of a series is likely to be much less than the variation between two randomly selected instances of a study. In addition, DICOM enforces that all instances in a series are of the same modality type such as CT. Therefore a mixed modality study such as PET/CT will have a series for the PET instances and a series for the CT instances. Accordingly, the blind use of data from different series without regard to what data has been requested by the user, can result in inefficient generation of the common values. In addition, sometimes a user operating a client does not request an entire study but rather requests only a portion of a study. If, for example, a small number of instances is requested, it is likely that the requested instances will be from the same series or adjacent series. Accordingly, generating a blob on a series level allows for data to be transmitted more efficiently given that the data for an entire study need not be transmitted for smaller requests. In addition, this can allow for more accurate data to be produced because it only takes into account the instances in the series.

At 212, image server 10 begins to transmit the common set of values to client 20. In some embodiments, image server 10 transmits the common set of values by streaming them in a byte stream to client 20.

At 214, image server 10 begins to transmit the per-instance data. The per-instance data are values of particular instances that are different than the common values.

At 216, image server 10 loads additional instances of the set of instances for which metadata has been requested.

At 218, image server 10 transmits the per-instance data of the newly loaded instances.

At 220, if all the instances have been loaded and processed, then the process ends. If not, then the process continues by, for example, proceeding again to 216.

Figure 3:
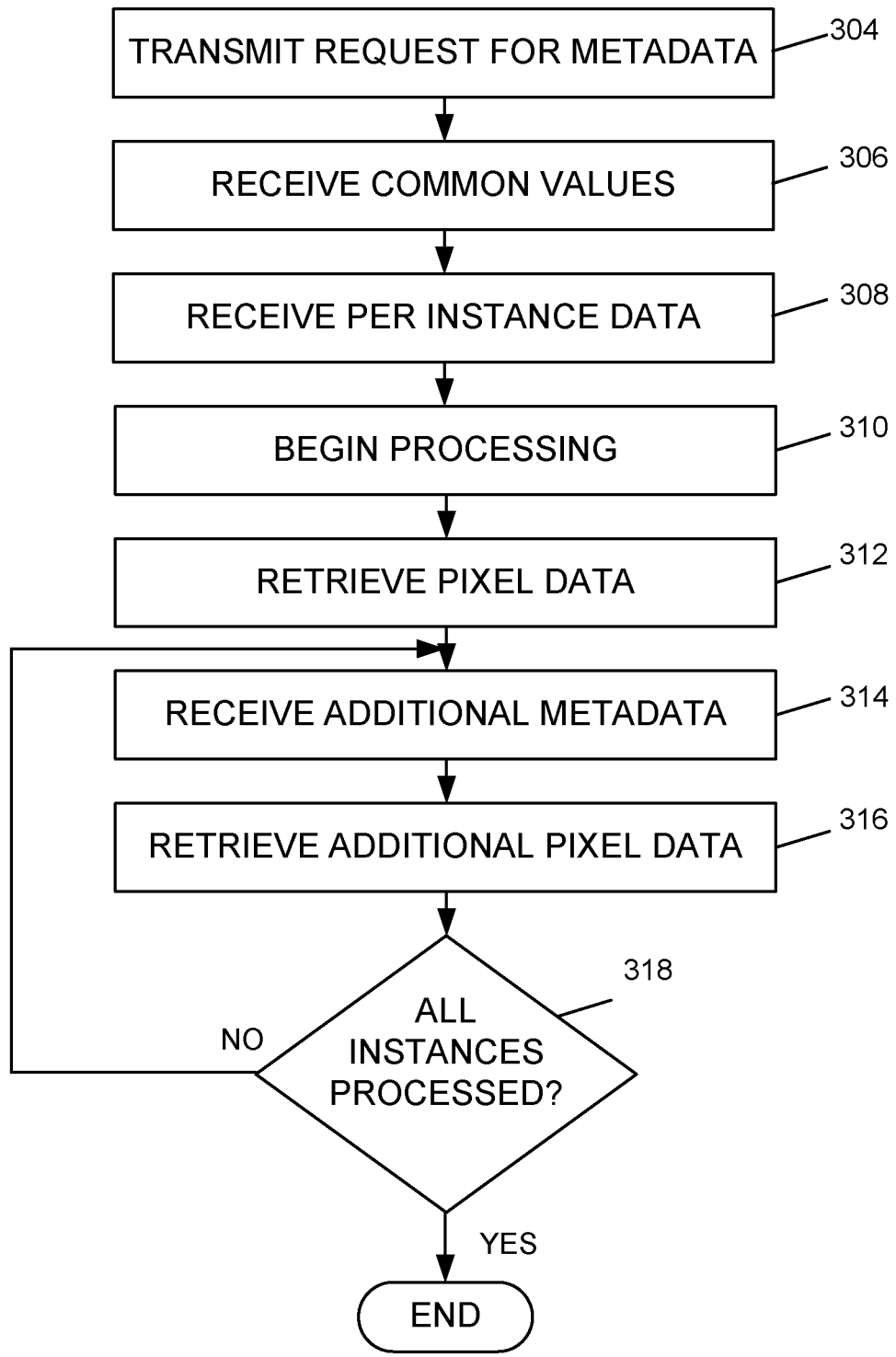
FIG. 3 is a flowchart illustrating a process by which the client of FIG. 1 performs metadata retrieval, according to various embodiments.

Reference is now made to FIG. 3, which illustrates a flowchart diagram of the process by which client 20 performs metadata retrieval and processes the retrieved metadata.

At 304, client 20 transmits a request to image server 10 for metadata. As mentioned above, in some embodiments, the requested metadata is for a set of DICOM instances.

At 306, client 20 receives the common values generated at 210 and transmitted at 212 of FIG. 2.

At 308, client 20 receives the per-instance data.

At 310, client 20 begins processing the data that has been received. For example, although not all of the data has been received, client 20 can begin initializing the application for displaying the instances. This can begin even before any of the pixel data has been received. For example, processing parameters and rendering parameters are used by client 20 to, for example, appropriately process the instances and to set up the screen correctly for viewing the instances. Examples of parameters include, but are not limited to, the modality used to generate the instances, slice thickness, procedure definition, body part examined, orientation of instances (cross section/laterality etc). Not all of these parameters will be applicable in every case. For example, some instances may not be individual slices and therefore there may not be any slice thickness, for example, MG (mammography) images are not "slices" but are simply different views. Even for magnetic resonance imaging (MRI), the scouts instances are not slices and therefore do not have a slice thickness. Different types of studies have different parameters. For example, CT has radiation but MR does not). These parameters are included in DICOM tags. However, which tags are of interest can vary greatly based on the modality and/or the procedure definition.

At 312, client 20 retrieves pixel data by, for example, transmitting a request to image server 10. In some embodiments, the pixel data that is requested corresponds to the instances for which metadata has been already received.

At 314, client 20 receives additional metadata (e.g. per-instances data) from image server 10.

At 316, client 20 retrieves additional pixel data, for example, transmitting a request to image server 10. In some embodiments, the requested pixel data corresponds to instances for which metadata was received at 314.

It should be understood that the flowcharts of FIGS. 2 and 3 do not necessarily require a particular order for all of their elements. In particular, in some embodiments, certain elements of each of the figures can be performed in parallel. In some embodiments, certain elements of FIGS. 2 and 3 can be performed in an order different than that shown.

In various embodiments, the metadata and pixel data can be retrieved in parallel. For example, referring again to FIG. 3, pixel data is retrieved at 312 and 316 as metadata is being retrieved and processed. In particular, 308 to 316 of FIG. 3 may overlap in time and may be executed in parallel or in a different order. Typically the client starts by retrieving the metadata blob and while doing that, in parallel the client can start the retrieval of the pixel data. This is in contrast to known systems where the retrieval metadata and pixel data is performed as a serialized workflow. Common orders are to read an entire metadata/pixel data object and then the next one in order, or to read the entire metadata for all objects and then read the pixel data as required, often not serially but several at a time.

In various embodiments when retrieving instances from third party PACS, the client displays the first instance before the last instances arrives from the third party PACS at the local server to which client 20 is coupled. An alternative representation of the process flow for client 20 according to some embodiments can be described as follows:

(1) Retrieve common values (this can include transmitting a request for metadata);

(2) Initiate retrieval of per-instance values (this can correspond to the difference values described above);

(3) Setup the display according to retrieved metadata (e.g. common values or common values and per-instance values);

(4) Initiate retrieval of pixel data; and (5) Revise setup of the display;

In various embodiments, (2) and (4) in the above process flow are ongoing in that retrieval of the data continues after it has been initiated until all the data is received. In addition, the retrieval can be done in a parallel manner such that (2) and (4) can be said to be executed in parallel even if they are initiated at different times (in some embodiments they are started almost simultaneously). In some embodiments, (4) is initiated prior to (2). In addition, (5) can be executed as needed on an ongoing basis throughout the process.

In some embodiments, this can reduce memory usage as well as the time to start sending data to $O(1)$ as apposed to the $O(m)$ achieved by known system. In various embodiments, the reduction from $O(m)$ objects to $O(1)$ object occurs because instead of sending 1 object for every image, a single object is sent for all m images, or one object per series is sent, with typically (in some embodiments) less than 10 series even as the number of images grows. In order to better understand the reduction from O(m) objects to O(1) assume a constant n, say 2, then the time to start sending the first object is the time taken to open the first two objects and create the common values. This is a constant amount of time assuming DICOM objects with the series are like each other (which is generally true). The total time to transmit the entire different object is still O(m) as all m objects need to be opened and sent. Memory usage/transmission size requires a few additional assumptions. Assume that for the average series there are lots of common attributes and a very few per-instance attributes, that is the size (common DICOM metadata)>>size (per-instance attributes). One can then effectively replace the size of the per-instance attributes with 0 and the size of the overall objects is O(1)—a constant determined by the size of the common attributes. In practice, this is not quite true, as the per-instance size is not actually 0, but it is close enough that we can use a reasonable size such as 200 k as the "constant" size. An analogous argument is made for performance/retrieve times from disk.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of retrieving metadata stored on a storage medium, the method comprising:
in response to a request from a client for metadata for a set of DICOM instances, the set of DICOM instances having a number, loading, at a server, n DICOM instances of the set of requested DICOM instances, where n is less than the number of the set of DICOM instances;
comparing, at the server, the metadata of the n loaded DICOM instances to each other;
generating, at the server, a common set of values of the metadata of the n loaded DICOM instances based on the comparison of the n loaded DICOM instances;
streaming the common set of values from the server to the client;
for each of the requested DICOM instances:
loading the DICOM instance at the server, if not already loaded;
determining per-instance data for the DICOM instance at the server, the per-instance data being a difference between the metadata of the DICOM instance and the common set of values of the metadata of the n DICOM instances; and
transmitting the per-instance data of the DICOM instance from the server to the client.

2. The method of claim 1, wherein the common values are generated as a binary large object (blob).

3. The method of claim 1, wherein the n instances correspond to a series.

4. The method of claim 1, wherein the n instances correspond to a sub-series.

5. The method of claim 1, wherein the n instances exclude an unusual instance.

6. The method of claim 1, wherein the n instances exclude a localizer image.

7. The method of claim 1, wherein the n instances exclude a scout image.

8. The method of claim 1, wherein the transmission of the per-instance data of the n loaded DICOM instances to the client is initiated prior to loading of the additional DICOM instances.

9. The method of claim 1, further comprising:
receiving a request for pixel data from the client; and
transmitting pixel data to the client.

10. The method of claim 1, further comprising, at the client:
receiving the set of common values;
receiving the per-instance data;
initiating a display based on the common values;
receiving pixel data; and
displaying the pixel data.

11. A non-transitory computer-readable storage medium encoded with instructions that cause a processor to perform a method retrieving metadata stored on a storage medium according to claim 1.

12. A server for use in retrieval of metadata stored on a storage medium, the server comprising:
a processor, the processor configured to:
in response to a request from a client for metadata for a set of DICOM instances, the set of DICOM instances having a number, load, at the server, n DICOM instances of the set of requested DICOM instances, where n is less than the number of the set of DICOM instances;
compare the metadata of the n loaded DICOM instances to each other at the server;
generate a common set of values of the metadata of the n loaded DICOM instances based on the comparison of the n loaded DICOM instances;
stream the common set of values from the server to the client;
for each of the requested DICOM instances:
load the DICOM instance at the server, if not already loaded;
determine per-instance data for the DICOM instance at the server, the per-instance data being a difference between the metadata of the DICOM instance and the common set of values of the metadata of the n DICOM instances; and transmit the per-instance data of the DICOM instance from the server to the client.

13. The server of claim 12, wherein the common values are generated as a binary large object (blob).

14. The server of claim 12, wherein the n instances correspond to a series.

15. The server of claim 12, wherein the n instances correspond to a sub-series.

16. The server of claim 12, wherein the n instances exclude an unusual instance.

17. The server of claim 12, wherein the n instances exclude a localizer image.

18. The server of claim 12, wherein the n instances exclude a scout image.

19. The server of claim 12, wherein the processor is further configured to initiate the transmission of the per-instance data of the n loaded DICOM instances to the client prior to loading of the additional DICOM instances.

20. The server of claim 12, wherein the processor is further configured to:
receive a request for pixel data from the client; and
transmit pixel data to the client.

* * * * *